United States Patent [19]

Schott et al.

[11] Patent Number: 4,604,129
[45] Date of Patent: Aug. 5, 1986

[54] INFLUENCING PLANT GROWTH

[75] Inventors: Eberhard P. Schott, Neustadt; Volker Fischer, Wessental; Johann Jung, Limburgerhof; Henning Rosebrock, Stetten, all of Fed. Rep. of Germany

[73] Assignee: BASF Aktiengesellschaft, Fed. Rep. of Germany

[21] Appl. No.: 640,237

[22] Filed: Aug. 14, 1984

Related U.S. Application Data

[63] Continuation of Ser. No. 388,516, Jun. 15, 1982, abandoned.

[30] Foreign Application Priority Data

Jun. 23, 1981 [DE] Fed. Rep. of Germany ....... 3124497

[51] Int. Cl.$^4$ ............................................. A01N 43/90
[52] U.S. Cl. ............................................ 71/76; 71/90; 71/92
[58] Field of Search ........................................ 71/76, 92

[56] References Cited

U.S. PATENT DOCUMENTS

| | | | |
|---|---|---|---|
| 3,865,570 | 2/1975 | George et al. | 71/76 |
| 4,049,418 | 9/1977 | Timmler et al. | 71/76 |
| 4,055,409 | 10/1977 | Johnson et al. | 71/76 |
| 4,170,462 | 10/1979 | O'Neal | 71/76 |
| 4,189,434 | 2/1980 | Platz et al. | 71/76 |
| 4,268,300 | 5/1981 | Platz et al. | 71/76 |
| 4,282,027 | 8/1981 | Platz et al. | 71/76 |
| 4,310,345 | 1/1982 | Platz et al. | 71/76 |

Primary Examiner—Catherine L. Mills
Attorney, Agent, or Firm—Keil & Weinkauf

[57] ABSTRACT

A process for regulating plant growth, wherein the plants, the seed or the soil are treated with a polycyclic nitrogen-containing compound of the formula

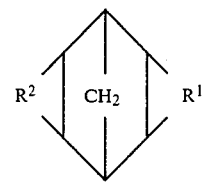

where $R^1$ is $-\underset{\underset{R^3}{|}}{N}-$ or $-N=N-\underset{\underset{R^3}{|}}{N}-$, $R^2$ is $-N=N-$ or $-NH-NH$, and $R^3$ is

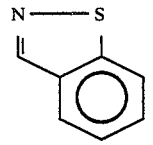

or phenyl which is substituted by halogen, fluoroalkyl of 1 to 2 carbon atoms, $NO_2$ or $C_1-C_3$-alkyl, the equivalent of less than 100 g of active ingredient being employed per hectare.

5 Claims, No Drawings

INFLUENCING PLANT GROWTH

This application is a continuation of application Ser. No. 388,516, filed on June 15, 1982, abandoned.

The present invention relates to a process for influencing the growth of plants, for example of rice or ornamentals, by treating the plants, the seed or the soil with a polycyclic nitrogen-containing organic compound. When employed on plants which thrive in an arid climate, the process also has a favorable influence on the water balance of the plants.

Our German Laid-Open Application DOS 2,615,878 (corresponding to GB Patent Specification No. 1,573,161) discloses the use of polycyclic nitrogen-containing organic compounds for influencing plant growth. The amount of the active ingredient specifically disclosed therein as being employed by hectare was from 100 g to 15 kg.

Because of the high cost of the said polycyclic compounds, these application rates are economically inviable.

When plants are grown from seed, the latter is conventionally sown in a special nursery bed, for example in a greenhouse. The seeds then germinate and develop into young plants, which are later removed from the nursery bed and transplanted to their final location. The young plants must not be too small or too large when transplanted, and this operation must therefore be carried out at a particular stage, determined by experience, in their growth.

Frequently, when the plants are due to be transplanted into the open, this operation is impossible, for example owing to unfavorable weather conditions. The young plants continue to grow, are too large when transplanted later, and are more susceptible to the shock of transplantation. In addition, mechanized planting out of plants is technically no longer possible with plants which are too large.

The rigor of cereal plants, i.e. rice, depends, inter alia, on the length of the stems. A reduction in this length reduces the corresponding leverage and thus the danger of static breakage of stems. The risk of lodging in cereal crops is diminished.

In the cultivation of ornamentals, compact plants are preferred to plants which are too large or too bulky. Compactness increases, for example, the number of plants per unit area of the greenhouse or the ratio of the size of the blossom to the size of the shoot, and thus the market quality.

A further object of the invention is to influence the growth of plants in such a way that they thrive better and/or use less water where water is scarce, i.e., in an arid climate.

Saving water is not only in aim in itself in areas where water is scarce—is also counteracts the salinification of the surface of the soil by evaporation.

In addition to well-known farming techniques, e.g., the dry farming system, attempts are also being made to save water by influencing the transpiration of crop plants. A reduction in transpiration, especially in broadleaved plants, e.g., vines, can be achieved by spraying them with film-forming substances (polymers, paraffin) (U.S. Pat. Nos. 3,676,102 and 3,339,373). However, as this process interferes with the function of the stomata, which are essential for gaseous interchange, the formation of green material by the crop plants is frequently reduced because the growth of the plants is hindered.

Apart from this, narrow-leaved plants are not as suitable for such a treatment because their leaf area is smaller than that of broadleaved plants and because only a small amount of film-forming material adheres to the narrow leaves.

We have found that a polycyclic nitrogen-containing compound of the formula

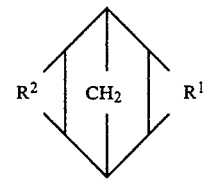

where $R^1$ is $-\underset{R^3}{\underset{|}{N}}-$ or $-N=N-\underset{R^3}{\underset{|}{N}}-$, $R^2$ is $-N=N-$ or $-NH-NH$, and $R^3$ is

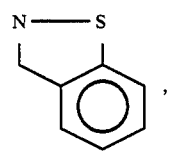

or phenyl which is substituted by halogen, fluoroalkyl of 1 to 2 carbon atoms, $NO_2$ or $C_1$-$C_3$-alkyl, regulates the growth of plants when the amount of active ingredient used per hectare is less than 100 g, preferably from 0.01 to 99 g, in particular from 0.01 to 90 g, in the treatment of the soil and an equivalent amount in the treatment of the plants or seed. It is particularly surprising that amounts at least one order of magnitude less than those previously recommended are effective.

It is thus possible, for example in the case of rice, to transplant high quality plants even when transplantation is delayed, or to increase the stability in the case of rice and the number of plants per unit area or the ratio of the size of the blossom to the size of the shoot in the case of ornamentals, and thus to increase the market quality. Furthermore, it is surprising that in spite of an initial inhibition of growth the physiological development of the young plants accelerates after transplantation. At the time of transplantation, treated plants are compact and strong, and show a higher rate of growth. After transplantation, they are, in comparison to untreated plants, therefore better able to withstand the shock of transplantation, have an increased resistance to unfavorable weather conditions, and develop more rapidly. These advantages are also useful when there is no delayed transplantation. It is therefore possible quite generally to treat, according to the invention, the plants, the soil in which the young plants grow or in which the seed is sown, or the seed from which the young plants are intended to grow. In contrast to untreated plants, treated plants fulfill the following requirements for high quality:

no excessively rapid growth at high temperatures before transplantation,
better rooting,
less sensitivity to frost, before and after transplantation,
greater resistance to the shock of transplantation,
more rapid rooting and tillering after transplantation, delayed withering (senescence) of the older leaves and leaf sheaves, and
more compact growth and smaller volume of individual plants.

A further effect is observed when the abovementioned amount is used for instance on Indian corn plants growing in areas where water is scarce.

An improvement in the utilization of water available to plants can be achieved for instance by reducing transpiration, and also by changing the ratio of root to shoot.

By "reducing transpiration", we mean a reduction in the amount of water, in gaseous form, leaving the surface of the crop plants.

When the correct rates of active ingredients are applied, there are no negative effects on growth and yield of crop plants. The active ingredients act not only when applied to the soil (root take-up—preemergence treatment), but also when applied to the foliage (postemergence treatment); treatment of the seed can also have the desired effect. Whereas preemergence treatment is especially to be recommended in areas with a permanent scarcity of water, postemergence treatment is particularly suitable where, in temporary periods of drought, an individual application with variable timing is preferred.

Information on the formulations which can be used and the methods of application is given in the publications mentioned above and can be used in the process of the present invention.

The Examples which follow illustrate the efficacy of the process according to the invention.

I. Interaction between the amount used and the biological action

EXAMPLE 1

Seed of rice of the Tainung 67 variety was treated by dip-dressing in a dispersion of the active ingredient in water for 24 hours at 30° C. Sowing in seedling trays was carried out on 6 days later and emergence occurred 2 days afterwards. 13 and 21 days after sowing, the height of growth and the rate of growth were determined, and the following data were obtained:

|  | Days after sowing | Active ingredient g/hectare (concentration of active ingredient in the dressing liquid in ppm) | | |
|---|---|---|---|---|
|  |  | Untreated | Substance A | |
|  |  | 0 | 0.5 (5) | 1.0 (10) |
| Height of growth cm | 13 | 8.5 | 6.9 | 6.4 |
| Height of growth cm | 21 | 9.0 | 8.0 | 7.5 |
| Rate of growth % | 21 | 5.9 | 15.9 | 17.2 |
|  |  | [(9.0–8.5): 8.5 × 100 = 5.9%] | | |

Substance A = 5-(4-Chlorophenyl)-3,4,5,9,10-pentaazatetracyclo-[5,4,1,0$^{2,6}$,0$^{8,11}$]-dodeca-3,9-diene

EXAMPLE 2

Seed of rice of the Kaohshing 141 variety was treated by dip-dressing for 24 hours at 30° C. Sowing in seedling trays was carried out 6 days later and emergence occurred 2 days afterwards. 13 and 21 days after sowing, the height of growth and the rate of growth were determined, and the following data were obtained:

|  | Days after sowing | Active ingredient g/hectare ppm | | |
|---|---|---|---|---|
|  |  | Untreated | Substance A | |
|  |  | 0 | 0.5 (5) | 1.0 (10) |
| Height of growth cm | 13 | 10.5 | 8.5 | 7.0 |
| Height of growth cm | 21 | 11.2 | 10.2 | 9.5 |
| Rate of growth % | 21 | 6.7 | 20.0 | 35.7 |

EXAMPLE 3

Seed of rice of the Tainan 5 variety was treated by dip-dressing for 24 hours at 30° C. Sowing in seedling trays was carried out 5 days later and emergence occurred 2 days afterwards. 13 and 21 days after sowing, the height of growth was measured, and the following data were obtained:

|  | Days after sowing | Active ingredient g/hectare | | | |
|---|---|---|---|---|---|
|  |  | Untreated | Substance A | | |
|  |  | 0 | 0.25 (2.5) | 0.5 (5) | 1.0 (10) |
| Height of growth cm | 13 | 9.2 | 6.9 | 5.8 | 5.3 |
| Height of growth cm | 21 | 10.1 | 9.0 | 8.5 | 7.9 |
| Rate of growth % | 21 | 9.8 | 30.4 | 46.6 | 49.1 |

EXAMPLE 4

Seed of rice of the Inabawase variety was treated by dip-dressing for 24 hours at 30° C. Sowing in seedling trays was carried out 1 day later and emergence was observed 2 days afterwards. 7, 9, 13, 19 and 28 days after sowing, the height of growth and the rate of growth were determined, and 28 days after sowing the leaf weight and root weight per plant were determined. The following results were obtained:

|  | Days after sowing | Active ingredient g/hectare (ppm) | | |
|---|---|---|---|---|
|  |  | Untreated | Substance A | |
|  |  | 0 | 1 (10) | 10 (100) |
| Height of growth cm | 7 | 6.0 | 3.4 | 1.6 |
| Height of growth cm | 9 | 6.0 | 4.4 | 2.8 |
| Rate of growth % | 9 | 0.0 | 29.4 | 75.0 |
| Height of growth cm | 13 | 8.2 | 6.5 | 3.8 |
| Rate of growth % | 13 | 36.8 | 47.7 | 35.7 |
| Height of growth cm | 19 | 15.5 | 11.0 | 7.5 |
| Rate of growth % | 19 | 89.0 | 69.2 | 97.4 |
| Height of growth cm | 28 | 15.8 | 12.0 | 7.8 |
| Rate of growth % | 28 | 1.9 | 9.1 | 4.0 |
| Leaf weight DM mg/plant | 28 | 1.11 | 0.97 | 0.62 |
| Root weight DM mg/plant | 28 | 1.16 | 1.11 | 1.0 |
| Root weight: leaf weight DM | 28 | 1.04:1 | −1.14:1 | 1.61:1 |

DM = dry material

EXAMPLE 5

Seed of rice of the Nihonbare variety was sown. By the 19th day afterwards the plants had developed to the stage of the 3rd to 4th true leaf and the foliage was sprayed with 250 liters per hectare. The height of growth was measured 6 and 13 days after spraying, and the following data were obtained:

|  | Days after treatment | Active ingredient g/hectare (ppm) | |
| --- | --- | --- | --- |
|  |  | Untreated 0 | Substance A 0.0125 (0.05) |
| Height of growth cm | 6 | 28.0 | 24.0 |
| Height of growth cm | 13 | 32.0 | 26.0 |
| Rate of growth % | 13 | 14.3 | 8.3 |

It can be seen from Examples 1 to 5 that Substance A used in amounts of from 0.0125 g per hectare (0.05 ppm) to 1 g per hectare (10 ppm) leads to substantial inhibition of the growth in length, regardless of the variety. It is surprising that even 0.0125 g per hectare (0.05 ppm) leads to a 19.0% inhibition of growth 13 days after treatment.

The initial inhibition of growth after seed dressing is followed by a substantial increase in the rate of growth compared to untreated plants. This is associated with a considerably increased root:leaf weight ratio of 1.14–1.61:1 compared to about 1:1 in the case of untreated rice plants.

Controlled growth of young plants is thus achievable by seed dip-dressing using Substance A in amounts of from 0.25 g per hectare (2.5 ppm) to 1 g per hectare (10 ppm), and higher amounts up to 100 g per hectare (1,000 ppm) are also effective. Young plants which have been thus treated are more robust and more resistant at the time of transplantation into the open, and develop more rapidly after transplantation than rice plants from untreated seed.

Leaf treatment with Substance A reduces the length of stems and can thereby increase the stability.

EXAMPLE 6

Seed of rice of the Nihonbare variety was dressed for 24 hours at 30° C. in a bath containing Substance A. Sowing in seedling trays was carried out 6 days later, emergence occurred 2 days afterwards and the plants were transplanted into the open 24 days after sowing. 19 days after sowing the height of growth was measured, 16 and 22 days after transplantation the height of growth was measured and the number of tillering shoots was counted, and 22 days after transplantation the root length per plant and the leaf weight and root weight per plant were also determined.

This Example shows that the rice plants whose seed was treated with Substance A have reached the ideal height of growth of about 13 cm at the time of transplantation into the open, whereas the untreated plants have exceeded this height by far at this point in time, and are useless for planting out.

16 and 22 days after transplantation, the treated rice plants have attained and exceeded the height of growth of the untreated plants.

|  | Days after sowing | Active ingredient g/hectare (ppm) | | | |
| --- | --- | --- | --- | --- | --- |
|  |  | Untreated 0 | Substance A 0.5 (5) | 0.75 (7.5) | 1.0 (10) |
| Height of growth cm | 19 | 19.3 | 12.7 | 10.5 | 9.7 |
| Height of growth cm | 40 | 40.0 | 37.3 | 39.3 | 43.5 |
| Rate of growth % | 40 | 107.2 | 193.7 | 274.3 | 348.4 |
| Height of growth cm | 46 | 46.7 | 46.5 | 47.2 | 54.2 |
| Rate of growth % | 46 | 16.8 | 24.7 | 20.1 | 24.6 |
| Tillering shoots, number/plant | 40 | 3.2 | 3.7 | 4.3 | 4.3 |
| Tillering shoots, number/plant | 46 | 6.0 | 7.5 | 9.2 | 9.2 |
| Root length mm/plant | 46 | 170.8 | 162.5 | 176.8 | 200.8 |
| Leaf weight DM mg/plant | 46 | 84.5 | 84.5 | 99.5 | 109.0 |
| Root weight DM mg/plant | 46 | 33.5 | 31.0 | 34.5 | 43.5 |
| Root weight:leaf weight DM | 46 | 0.40:1 | 0.37:1 | 0.35:1 | 0.40:1 |

This accelerated development after transplantation is also exhibited by the treated plants with respect to the number of tillering shoots, the root length and the dry material weight.

Rice plants treated with Substance A are compact and in a strong condition at the time of transplantation. They withstand the shock of transplantation into the open better and subsequently develop more rapidly.

II. Interaction between the method of use and the biological action

EXAMPLE 7

Seed of rice of the Inabawase variety was treated by dip-dressing for 24 hours at 30° C. Sowing in seedling trays was carried out 1 day later, and emergence was observed 2 days afterwards. 7, 9, 13, 19 and 28 days after sowing, the height of growth and the rate of growth were determined, and 28 days after sowing the leaf weight and root weight per plant were determined. The following results were obtained:

|  | Days after sowing | Active ingredient g/hectare (ppm) | | | | |
| --- | --- | --- | --- | --- | --- | --- |
|  |  | Untreated 0 | Substance A 1 (10) | 10 (100) | Substance B 1 (10) | 10 (100) |
| Height of growth cm | 7 | 6.0 | 3.4 | 1.6 | 3.9 | 2.2 |
| Height of growth cm | 9 | 6.0 | 4.4 | 2.8 | 5.0 | 3.2 |
| Rate of growth % | 9 | 0.0 | 29.4 | 75.0 | 28.2 | 45.4 |
| Height of growth cm | 13 | 8.2 | 6.5 | 3.8 | 7.2 | 4.8 |
| Rate of growth % | 13 | 36.7 | 47.7 | 35.7 | 44.0 | 50.0 |
| Height of growth cm | 19 | 15.5 | 11.0 | 7.5 | 12.2 | 8.8 |
| Rate of growth % | 19 | 89.0 | 69.2 | 97.4 | 69.4 | 83.3 |
| Height of growth cm | 28 | 15.8 | 12.0 | 7.8 | 12.2 | 8.8 |
| Rate of growth % | 28 | 1.9 | 9.1 | 4.0 | 0 | 0 |
| Leaf weight DM mg/plant | 28 | 1.11 | 0.97 | 0.62 | 0.89 | 0.78 |
| Root weight DM mg/plant | 28 | 1.16 | 1.11 | 1.0 | 1.2 | 1.13 |

| | Days after sowing | Active ingredient g/hectare (ppm) | | | | |
|---|---|---|---|---|---|---|
| | | Untreated | Substance A | | Substance B | |
| | | 0 | 1 (10) | 10 (100) | 1 (10) | 10 (100) |
| Root weight:leaf weight DM | 28 | 1.04:1 | 1.14:1 | 1.16:1 | 1.35:1 | 1.45:1 |

Substance B = 5-(4-Bromophenyl)-3,4,5,9,10-pentaazatetracyclo-[5,4,1,0$^2$,0$^{8,11}$]-dodeca-3,9-diene

EXAMPLE 8

Seed of rice of the Inabawase variety was dressed with Substances And and B in the form of a slurry in water. Sowing in seedling trays was carried out the same day, and emergence occurred 2 days afterwards. 8, 10, 14, 20 and 29 days after sowing, the height of growth and the rate of growth were determined, and 29 days after sowing the leaf weight and root weight per plant were determined. The following experimental results were obtained:

| | Days after sowing | Active ingredient g/hectare (ppm) | | | | |
|---|---|---|---|---|---|---|
| | | Untreated | Substance A | | Substance B | |
| | | 0 | 1 (10) | 10 (100) | 1 (10) | 10 (100) |
| Height of growth cm | 8 | 5.6 | 1.8 | 0.5 | 2.8 | 0.8 |
| Height of growth cm | 10 | 6.8 | 2.2 | 0.9 | 3.4 | 1.4 |
| Rate of growth % | 10 | 21.4 | 22.2 | 80.0 | 21.4 | 75.0 |
| Height of growth cm | 14 | 9.1 | 2.6 | 1.1 | 5.0 | 1.9 |
| Rate of growth % | 14 | 33.8 | 18.2 | 22.2 | 47.0 | 35.7 |
| Height of growth cm | 20 | 16.2 | 4.2 | 2.4 | 8.5 | 2.8 |
| Rate of growth % | 20 | 78.0 | 61.5 | 118.2 | 70.0 | 47.4 |
| Height of growth cm | 29 | 17.5 | 5.8 | 3.1 | 9.8 | 3.5 |
| Rate of growth % | 29 | 8.0 | 38.1 | 29.2 | 1.53 | 25.0 |
| Leaf weight DM mg/plant | 29 | 1.13 | 0.76 | 0.42 | 0.81 | 0.31 |
| Root weight DM mg/plant | 29 | 1.4 | 1.36 | 1.14 | 1.3 | 1.1 |
| Root weight:leaf weight DM | 29 | 1.24:1 | 1.79:1 | 2.71:1 | 1.6:1 | 3.55:1 |

EXAMPLE 9

Substances A and B, in the form of a slurry in water, were flushed into the soil before sowing, but were not worked in. Thereafter, on the same day, seed of rice of the Inabawase variety was sown, and emergence was observed two days afterwards. 8, 10, 14, 20 and 29 days after sowing, the height of growth and the rate of growth were determined, and the 29th day after sowing the leaf weight and root weight per plant were determined. The following results were obtained:

| | Days after sowing | Active ingredient g/hectare (ppm) | | | | |
|---|---|---|---|---|---|---|
| | | Untreated | Substance A | | Substance B | |
| | | 0 | 1 (10) | 10 (100) | 1 (10) | 10 (100) |
| Height of growth cm | 8 | 5.0 | 1.8 | 0.1 | 2.2 | 0.5 |
| Height of growth cm | 10 | 6.0 | 2.4 | 0.5 | 2.8 | 1.5 |
| Rate of growth % | 10 | 20.0 | 33.3 | 400.0 | 27.3 | 200.0 |
| Height of growth cm | 14 | 8.2 | 3.0 | 0.5 | 3.2 | 1.5 |
| Rate of growth % | 14 | 36.7 | 25.0 | 0.0 | 14.3 | 0.0 |
| Height of growth cm | 20 | 13.8 | 4.5 | 0.5 | 5.5 | 3.5 |
| Rate of growth % | 20 | 68.3 | 50.0 | 0.0 | 71.9 | 133.3 |
| Height of growth cm | 29 | 15.5 | 6.0 | 0.5 | 7.2 | 3.5 |
| Rate of growth % | 29 | 12.3 | 33.3 | 0.0 | 30.9 | 0.0 |
| Leaf weight DM mg/plant | 29 | 1.14 | 0.31 | <0.01 | 0.4 | 0.11 |
| Root weight DM mg/plant | 29 | 1.12 | 0.98 | 1.24 | 0.96 | 0.96 |
| Root weight:leaf weight DM | 29 | 0.98:1 | 3.16:1 | >124:1 | 2.40:1 | 8.73:1 |

< = less than
> = greater than

EXAMPLE 10

Substances A and B, in the form of a slurry, were sprayed onto the surface of the soil before sowing, and worked into the soil. Rice of the Inabawse variety was sown 1 day later, and emergence occurred 2 days afterwards. 7, 9, 13 and 28 days after sowing, the height of growth and the rate of growth were determined, and on the 28th day after sowing the leaf weight and root weight per plant were determined. The following experimental results were obtained:

| | Days after sowing | Active ingredient g/hectare (ppm) | | | | |
|---|---|---|---|---|---|---|
| | | Untreated | Substance A | | Substance B | |
| | | | 1 (10) | 10 (100) | 1 (10) | 10 (100) |
| Height of growth cm | 7 | 6.0 | 3.2 | 0.5 | 4.0 | 2.0 |
| Height of growth cm | 9 | 6.1 | 3.4 | 0.8 | 4.6 | 2.5 |
| Rate of growth % | 9 | 1.6 | 6.2 | 60.0 | 15.0 | 25.0 |
| Height of growth cm | 13 | 8.8 | 3.5 | 1.0 | 4.8 | 2.5 |
| Rate of growth % | 13 | 44.3 | 2.9 | 25.0 | 4.3 | 0.0 |
| Height of growth cm | 19 | 15.2 | 7.5 | 2.6 | 9.2 | 4.8 |

-continued

|  | Days after sowing | Active ingredient g/hectare (ppm) | | | | |
|---|---|---|---|---|---|---|
|  |  | Untreated | Substance A | | Substance B | |
|  |  |  | 1 (10) | 10 (100) | 1 (10) | 10 (100) |
| Rate of growth % | 19 | 72.7 | 114.3 | 160.0 | 91.7 | 92.0 |
| Height of growth cm | 28 | 15.2 | 8.2 | 2.6 | 9.8 | 5.5 |
| Rate of growth % | 28 | 0.0 | 9.3 | 0.0 | 6.5 | 14.6 |
| Leaf weight DM mg/plant | 28 | 1.04 | 0.42 | 0.06 | 0.5 | 0.28 |
| Root weight DM mg/plant | 28 | 1.17 | 0.94 | 0.88 | 1.16 | 0.84 |
| Root weight:leaf weight DM | 28 | 1.12:1 | 2.24:1 | 14.7:1 | 2.32:1 | 3:1 |

EXAMPLE 11

Rice of the Inabawase variety was sown in seedling trays, and substances A and B, in the form of a slurry, were sprayed immediately after sowing onto the top layer of soil above the seeds, and lightly worked into the soil. Emergence was observed 2 days later. 8, 10, 14, 20 and 29 days after working into the soil, the height of growth and the rate of growth were determined, and on the 29th day after working into the soil the leaf weight and root weight per plant were determined. The results of the experiments are as follows:

|  | Days after sowing | Active ingredient g/hectare (ppm) | | | | |
|---|---|---|---|---|---|---|
|  |  | Untreated 0 | Substance A | | Substance B | |
|  |  |  | 1 (10) | 10 (100) | 1 (10) | 10 (100) |
| Height of growth cm | 8 | 6.0 | 2.2 | 0.1 | 2.9 | 0.5 |
| Height of growth cm | 10 | 6.5 | 2.2 | 0.5 | 3.2 | 1.0 |
| Rate of growth % | 10 | 8.3 | 0.0 | 400.0 | 10.3 | 100.0 |
| Height of growth cm | 14 | 8.2 | 2.5 | 0.5 | 3.5 | 1.0 |
| Rate of growth % | 14 | 26.2 | 13.6 | 0.0 | 9.4 | 0.0 |
| Height of growth cm | 20 | 14.0 | 4.8 | 0.9 | 7.5 | 1.9 |
| Rate of growth % | 20 | 70.7 | 92.0 | 80.0 | 114.3 | 90.0 |
| Height of growth cm | 29 | 15.2 | 5.5 | 1.8 | 8.8 | 1.9 |
| Rate of growth % | 29 | 8.6 | 14.6 | 100.0 | 17.3 | 0.0 |
| Leaf weight DM mg/plant | 29 | 1.09 | 0.53 | 0.02 | 0.59 | 0.16 |
| Root weight DM mg/plant | 29 | 1.10 | 1.07 | 1.21 | 0.99 | 1.13 |
| Root weight:leaf weight DM | 29 | 1.01:1 | 2.02:1 | 60.5:1 | 1.68:1 | 7.06:1 |

EXAMPLE 12

Rice of the Inabawase variety was sown in seedling trays and emergence occurred 2 days later. 8 days afterwards, when the plants were at the 11th stage of development, according to Zadoks (i.e., when the first leaf has unfolded), Substances A and B, in the form of a slurry in water, were flushed into the soil. 7 and 19 days after treatment, the height of growth and the rate of growth were determined, and on the 28th day the leaf weight and root weight per plant were determined. The following data were obtained:

|  | Days after sowing | Active ingredient g/hectare (ppm) | | | | |
|---|---|---|---|---|---|---|
|  |  | Untreated 0 | Substance A | | Substance B | |
|  |  |  | 1 (10) | 10 (100) | 1 (10) | 10 (100) |
| Height of growth cm | 7 | 12.5 | 12.5 | 12.0 | 12.8 | 12.5 |
| Height of growth cm | 19 | 14.8 | 15.0 | 14.2 | 15.2 | 14.0 |
| Rate of growth % | 19 | 18.4 | 20.0 | 18.3 | 18.8 | 12.0 |
| Leaf weight DM mg/plant | 28 | 1.13 | 1.07 | 1.01 | 1.14 | 0.99 |
| Root weight DM mg/plant | 28 | 1.15 | 1.16 | 1.14 | 1.22 | 1.17 |
| Root weight:leaf weight DM | 28 | 1.02:1 | 1.08:1 | 1.13:1 | 1.07:1 | 1.18:1 |

EXAMPLE 13

10 days after transplantation into pots, ie. at a height of growth of 5 cm, ornamentals of Impatiens walleriana of the Minette variety were treated by watering the total leaf surface with a slurry of the formulated active ingredient in water. 39 days after treatment, the height of growth was measured:

|  | Days after treatment | Active ingredient g/hectare (ppm) | | |
|---|---|---|---|---|
|  |  | Untreated 0 | Substance A | |
|  |  |  | 0.5 (5) | 2.5 (25) |
| Height of growth cm | 39 | 16.2 | 15.3 | 13.2 |
| Height of growth % | 39 | 100 | 94 | 81 |

EXAMPLE 14

28 days after pricking out, ie. at a height of growth of 5 cm, Tagetes erecta ornamentals of the Honey Comb and Golden Star varieties were treated by watering the total leaf surface. 39 days after treatment, the height of growth was measured;

| Variety | Days after treatment | Active ingredient g/hectare (ppm) | | |
|---|---|---|---|---|
|  |  | Untreated 0 | Substance A | |
|  |  |  | 0.5 (5) | 2.5 (25) |
| Golden Star |  |  |  |  |
| Height of growth cm | 39 | 16.7 | 16.3 | 14.5 |
| Height of growth % | 39 | 100 | 98 | 87 |
| Honey Comb |  |  |  |  |
| Height of growth cm | 39 | 16.2 | 15.1 | 13.2 |

-continued

| Variety | Days after treatment | Active ingredient g/hectare (ppm) | | |
|---|---|---|---|---|
| | | Untreated 0 | Substance A 0.5 (5) | 2.5 (25) |
| Height of growth % | 39 | 100 | 93 | 81 |

It can be seen from Examples 13 and 14 that in both species of ornamental Substance A, in amounts of 0.5 and 2.5 g per hectare, causes inhibition of from 2 to 19% of the growth in length.

The cultivation of ornamentals can be carried out more economically, without adversely affecting the number of blossoms, by a high population density per unit area, due to the reduction in volume of the individual plants.

Examples 7 to 14 demonstrate that Substances A and B clearly inhibit the growth in length of rice plants and ornamentals. The method of use of Substances A and B is not critical, and the following methods can, for example, be used:

seed dip-dressing (Example 7),
slurry dressing (Example 8),
flushing into the soil before sowing, but without subsequent working into the soil (Example 9),
spraying onto the soil surface before sowing, followed by working into the soil (Example 10),
spraying the top layer of soil above the seeds after sowing, followed by light working into the soil (Example 11),
flushing into the soil after the young rice plant has developed the first true foliage leaf (Example 12),
leaf treatment by spraying (sic-erroneously Spülen, cf. Example 5) (Example 5), or
leaf treatment by watering (Examples 13 and 14).

The initially desired inhibition of growth from emergence to the time of transplantation of the rice plants into the open is replaced, from the 2nd week, by a stimulation of growth, which increases as the amount used increases. This phenomenon also continues into the period after transplantation, so that the treated rice plants develop more rapidly in the open.

This cessation of the originally desired inhibition of growth and the change to a desirable, later, more rapid development are partly caused by the root:leaf ratio of the treated plants. Compared with untreated plants having a ratio of from 0.98:1 to 1.12:1, the treated seedlings show a ratio of from 1.08:1 to greater than 124:1 about 4 weeks after application of Substance A, and a ratio of from 1.07:1 to 23.0:1 after Substance B.

III. Comparison of bioregulators of various chemical structures

EXAMPLES 15 to 17

Seed of rice of the Inabawase variety was treated by dip-dressing for 24 hours at 30° C. Sowing in seedling trays was carried out 1 day later, and emergence occurred 2 days afterwards. 7, 9, 13, 19 and 28 days after sowing, the height of growth and the rate of growth were determined, and 28 days after sowing the leaf weight and root weight per plant were determined. The following comparisons were made:

| | Days after sowing | Active ingredient g/hectare (ppm) | | | | |
|---|---|---|---|---|---|---|
| | | Untreated 0 | Substance A 1 (10) | Substance A 10 (100) | Substance C 10 (100) | Substance D 10 (100) | Substance E 10 (100) |
| Height of growth cm | 7 | 6.0 | 3.4 | 1.6 | 7.0 | 6.6 | 6.8 |
| Height of growth cm | 9 | 6.0 | 4.4 | 2.8 | 7.8 | 8.0 | 8.1 |
| Rate of growth % | 9 | 0.0 | 29.4 | 75.0 | 11.1 | 21.2 | 19.1 |
| Height of growth cm | 13 | 8.2 | 6.5 | 3.8 | 11.8 | 11.2 | 11.2 |
| Rate of growth % | 13 | 36.7 | 47.7 | 35.7 | 51.3 | 40.0 | 38.3 |
| Height of growth cm | 19 | 15.5 | 11.0 | 7.5 | 16.8 | 15.5 | 16.0 |
| Rate of growth % | 19 | 89.0 | 69.2 | 97.4 | 42.3 | 38.4 | 42.8 |
| Height of growth cm | 28 | 15.8 | 12.0 | 7.8 | 17.0 | 15.5 | 16.5 |
| Rate of growth % | 28 | 1.9 | 9.1 | 4.0 | 1.2 | 0.0 | 3.1 |
| Leaf weight DM mg/plant | 28 | 1.11 | 0.97 | 0.62 | 1.22 | 1.04 | 1.19 |
| Root weight DM mg/plant | 28 | 1.16 | 1.11 | 1.0 | 1.17 | 1.17 | 1.24 |
| Root weight:leaf weight DM | 28 | 1.04:1 | 1.14:1 | 1.61:1 | 0.96:1 | 1.12:1 | 1.04:1 |

Substance C = 2-Chloroethylphosphonic acid
Substance D = 1,1-Dimethylpiperidinium chloride
Substance E = Mixture of 2 parts (parts by weight) of 1,1-dimethylpiperidinium chloride and 1 part of 2-chloroethylphosphonic acid It can be seen from Examples 15 to 17 that, in contrast to Substance A, none of the three Substances C, D and E tested for comparison causes an inhibition of the growth in length of the young rice plants. A general stimulation of growth is observed in comparison with untreated plants.

Even in the root weight:leaf weight ratio, based on dry material, the plants treated with Substances C, D and E hardly differ from untreated plants.

EXAMPLES 18 to 20

Seed of rice of the Inabawase variety was treated, as before, with the active ingredients Substances A, C, D and E, by the slurry dressing method. Sowing in seedling trays was carried out the same day, and emergence occurred 2 days afterwards. 8, 10, 14, 20 and 28 days after sowing, the height of growth and the rate of growth were determined, and 29 days after sowing the leaf weight and root weight per plant were determined.

Even in this case, it was found that, in contrast to Substance A, none of the Substances C, D and E tested for comparison caused inhibition of the growth in length of the young rice plants. Results similar to those of Experimental Examples 15 to 17 were found.

|  | Days after sowing | Active ingredient g/hectare (ppm) | | | | | |
|---|---|---|---|---|---|---|---|
|  |  | Untreated 0 | Substance A 1 (10) | Substance A 10 (100) | Substance C 10 (100) | Substance D 10 (100) | Substance E 10 (100) |
| Height of growth cm | 8 | 5.6 | 1.8 | 0.5 | 6.2 | 6.5 | 7.1 |
| Height of growth cm | 10 | 6.8 | 2.2 | 0.9 | 8.1 | 7.8 | 9.0 |
| Rate of growth % | 10 | 21.4 | 22.2 | 80.0 | 30.6 | 20.0 | 26.8 |
| Height of growth cm | 14 | 9.1 | 2.6 | 1.1 | 10.6 | 10.8 | 11.9 |
| Rate of growth % | 14 | 33.8 | 18.2 | 22.2 | 30.9 | 38.5 | 32.2 |
| Height of growth cm | 20 | 16.2 | 4.2 | 2.4 | 16.2 | 16.5 | 16.2 |
| Rate of growth % | 20 | 78.0 | 61.5 | 118.2 | 52.8 | 52.8 | 36.1 |
| Height of growth cm | 29 | 17.5 | 5.8 | 3.1 | 17.0 | 17.0 | 16.8 |
| Rate of growth % | 29 | 8.0 | 38.1 | 29.2 | 4.9 | 3.0 | 3.7 |
| Leaf weight DM mg/plant | 29 | 1.13 | 0.76 | 0.42 | 1.13 | 1.72 | 1.40 |
| Root weight DM mg/plant | 29 | 1.40 | 1.36 | 1.14 | 1.40 | 1.44 | 1.26 |
| Root weight:leaf weight DM | 29 | 1.24:1 | 1.79:1 | 2.71:1 | 1.24:1 | 0.83:1 | 0.9:1 |

EXAMPLE 21

Indian corn seed of the 3369 A variety was wet-treated with active ingredient A (=5-(4-chlorophenyl)-3,4,5,9,10-pentaazatetracyclo-[5,4,1,0$^{2,5}$,0,$^{8,11}$]dodeca-3,9-diene), sown in the open and cultivated without water. 37 days after sowing, symptoms of wilting were observed, and the leaf water potential was ascertained 50 days after sowing by means of a pressure bomb.

The symptoms of wilting were clearly reduced as a result of the treatment, and the water potential of the foliage was increased.

There was no detectable influence on the plant population or on the number of cobs per plant.

By contrast, the number of kernels per cob, the weight of 1,000 kernels and the kernel yield per hectare were clearly increased as a result of the improved water utilization.

|  | Active ingredient A g/ha | | | |
|---|---|---|---|---|
|  | 0 | 0.21 | 2.1 | 21.0 |
| kernels/cob* |  |  |  |  |
| g | 74.9 | 87.1 | 99.8 | 98.9 |
| % | 100 | 116 | 133 | 132 |
| 1,000-kernel weight* |  |  |  |  |
| g | 232 | 235 | 242 | 250 |
| % | 100 | 101 | 104 | 108 |
| corn yield* |  |  |  |  |
| dt/ha | 50.6 | 58.7 | 57.9 | 56.1 |
| % | 100 | 116 | 114 | 111 |
| wilted leaves % | 50 | 51 | 38 | 14 |
| leaf water potential bar | 16.7 | — | — | 14.5 |

*calculated with reference to dry material

EXAMPLE 22

Indian corn seed of the 3369 A variety was wet-treated with active ingredient A, sown in the open, and cultivated without water. Symptoms of wilting and the height of these plants were assessed 31 days after sowing.

As in Example 1, the wilt symptoms of the treated plants were clearly reduced, compared with untreated plants. A considerable improvement in water utilization is ascertained here too. Furthermore, the treatment resulted in a 10 to 20% reduction in growth height.

|  | Active ingredient A g/ha | | | | | |
|---|---|---|---|---|---|---|
|  | 0 | 2.1 | 4.2 | 6.3 | 8.4 | 10.5 |
| wilted leaves % | 83.1 | 13.8 | 16.7 | 15.8 | 11.7 | 7.9 |

-continued

|  | Active ingredient A g/ha | | | | | |
|---|---|---|---|---|---|---|
|  | 0 | 2.1 | 4.2 | 6.3 | 8.4 | 10.5 |
| growth inhibition % | 0 | 9.3 | 9.9 | 13.9 | 18.6 | 20.1 |

EXAMPLE 23

Indian corn seed of the 3369 A variety was treated for 2 hours by dip-dressing, at 25° C., in a dispersion of active ingredient A in water. A batch of the same seed was treated in the same way with pure water.

The seed was then sown in the open, and the plants were cultivated without water.

The yield parameters were evaluated when the kernels were ripe. Here, too, yield factors were considerably improved.

What is striking is that the treated plants are, due to improved water availability, more resistant to diseases (*Ustilago scitaminea* in this instance). The number of healthy corn cobs was increased by treatment with active ingredient A.

|  | Active ingredient A g/ha | | | | | | |
|---|---|---|---|---|---|---|---|
|  | 0 | H$_2$O 0 | 0.1 | 0.3 | 0.9 | 2.7 | 27.0 |
| cob yield |  |  |  |  |  |  |  |
| dt/ha | 59.0 | 62.0 | 63.0 | 69.0 | 66.0 | 72.0 | 72.0 |
| % | 100 | 105 | 107 | 117 | 112 | 122 | 122 |
| yield of healthy cobs |  |  |  |  |  |  |  |
| dt/ha | 55.5 | 57.8 | 59.0 | 66.3 | 62.7 | 67.2 | 69.0 |
| % | 100 | 104 | 106 | 119 | 113 | 121 | 124 |
| 1,000-kernel weight |  |  |  |  |  |  |  |
| g | 268 | 287 | 281 | 290 | 286 | 294 | 312 |
| % | 100 | 107 | 105 | 108 | 107 | 110 | 116 |

Application may be effected for instance in the form of directly sprayable solutions, powders, suspensions, dispersions, emulsions, oil dispersions, pastes, dusts, broadcasting agents, or granules by spraying, atomizing, dusting, broadcasting or watering. The active ingredients may also be applied as a seed treatment. The forms of application depend entirely on the purpose for which the agents are being used.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

Oils of various types, herbicides, fungicides, nematicides, insecticides, bactericides, trace elements, fertilizers, antifoams (e.g., silicones) and bioregulators may be added to the individual active ingredients or mixtures thereof.

In various cases, combination or admixture with other growth-regulating active ingredients may be advantageous, e.g., with ethylene-forming compounds of different chemical structure (e.g., phosphonic acid derivatives, silanes and ethyl hydrazines), and onium compounds (e.g., trimethylammonium, hydrazonium and sulfonium salts, and derivatives of morpholinium, piperidinium and pyridazinium compounds). Of interest are also other growth-regulating compounds, inter alia from the group of trifluoromethylsulfonamido-p-acetotoluidides, maleic hydrazide, abscisic acid derivatives, triazole compounds, chlorinated phenoxy-fatty acids having an auxin-like action, and polyhydric alcohols and fatty acid esters having a specific action on meristematic tissue.

The amount of the agents according to the invention which is applied may vary, and depends mainly on the effect desired.

Application rates are generally from 0.01 to 99, and preferably from 0.01 to 30, g of active ingredient per hectare.

We claim:

1. A process for reducing the stem length of rice or Indian corn plants, which comprises: soaking the seeds of the plants in a dressing liquid containing an effective amount of a polycyclic, nitrogen-containing compound selected from the group consisting of 5-(4-chlorophenyl)-3,4,5,9,10-pentaazatetracyclo-[5,4,1,0$^{2,6}$,0$^{8,11}$]-dodeca-3,9-diene and 5-(4-bromophenyl)-3,4,5,9,10-pentaazatetracyclo-[5,4,1,0$^{2,6}$,0$^{8,11}$]-dodeca-3,9-diene, and thereafter planting the treated seeds.

2. The process of claim 1 wherein the polycyclic compound is 5-(4-chlorophenyl)-3,4,5,9,10-pentaazatetracyclo-[5,4,1,0$^{2,6}$,0$^{8,11}$]-dodeca-3,9-diene.

3. The process of claim 1, wherein the seed is rice seed.

4. The process of claim 1 wherein the polycyclic compound is 5-(4-chlorophenyl)-3,4,5,9,10-pentaazatetracyclo-[5,4,1,0$^{2,6}$,0$^{8,11}$]-dodeca-3,9-diene and the seeds are rice plant seeds.

5. The process of claim 1 wherein the polycyclic compound is 5-(4-chlorophenyl)-3,4,5,9,10-pentaazatetracyclo-[5,4,1,0$^{2,6}$,0$^{8,11}$]-dodeca-3,9-diene and the seeds are Indian corn plant seeds.

* * * * *